(12) United States Patent
Harrison et al.

(10) Patent No.: US 6,396,613 B1
(45) Date of Patent: May 28, 2002

(54) OPTICAL HIGH SPEED COMMUNICATIONS FOR A COMPUTED TOMOGRAPHY X-RAY MACHINE

(75) Inventors: Daniel David Harrison, Delanson; Deva Narayan Pattanayak, Niskayuna, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/218,638

(22) Filed: Dec. 22, 1998

(51) Int. Cl.[7] .............................. H04B 10/12
(52) U.S. Cl. ................... 359/173; 359/109; 359/142; 378/4; 385/24
(58) Field of Search ............... 359/173, 109, 359/142; 385/24, 31, 37; 378/4

(56) References Cited

U.S. PATENT DOCUMENTS

| | | | |
|---|---|---|---|
| 4,259,584 A | | 3/1981 | Krumme |
| 4,466,697 A | | 8/1984 | Daniel |
| 4,538,125 A | * | 8/1985 | Beckmann et al. ......... 333/248 |
| 4,796,183 A | * | 1/1989 | Ermert et al. .................. 378/4 |
| 5,029,336 A | | 7/1991 | Micheron et al. |
| 5,121,419 A | | 6/1992 | Micheron et al. |
| 5,530,422 A | | 6/1996 | Harrison ..................... 340/500 |
| 5,530,424 A | | 6/1996 | Harrison et al. ............ 340/500 |
| 5,535,033 A | | 7/1996 | Guempelein et al. |
| 5,978,438 A | * | 11/1999 | Resnick et al. ................ 378/4 |
| 6,108,483 A | | 8/2000 | Berkcan ..................... 385/147 |
| 6,301,324 B1 | * | 10/2001 | Pearson, Jr. et al. .......... 378/15 |

FOREIGN PATENT DOCUMENTS

| | | |
|---|---|---|
| DE | 43 42 778 | 6/1995 |
| EP | 0 188 085 | 7/1986 |
| EP | 0 594 089 | 4/1994 |
| FR | 2 440 041 | 5/1980 |
| FR | 2 600 879 | 8/1988 |
| WO | WO 98 53348 | 11/1998 |

* cited by examiner

*Primary Examiner*—Leslie Pascal
(74) *Attorney, Agent, or Firm*—John F. Thompson; Jill M. Breedlove

(57) ABSTRACT

A computed tomography system employs an optical communications link to reliably transmit high data rate data. The communications link comprises an optical emitter, an optical transmission line, a plurality of optical deflectors disposed randomly within the transmission line, and an optical receiver. The optical emitter is attached to the gantry of the computed tomography system and extends along the length of the gantry. The optical emitter generates a high data rate optical data signal, which travels along the optical transmission line in correspondence with data generated by detector array on the gantry. The plurality of optical deflectors causes portions the high data rate optical data signal to be internally reflected and subsequently refracted from the transmission line. The optical receiver disposed near the transmission line detects the portion of high data rate data refracted from the transmission line.

20 Claims, 8 Drawing Sheets

OPTICAL HIGH SPEED COMMUNICATIONS FOR A COMPUTED TOMOGRAPHY X-RAY MACHINE

BACKGROUND OF THE INVENTION

The present invention relates generally to computerized tomography (CT) communication, and more specifically to an optical communication system employed in a CT system.

CT systems typically employ a rotating frame or gantry to obtain multiple x-ray images, or views, at various rotational angles. Each set of images is identified as a "slice." A patient or object is generally positioned in a central opening on the rotating frame, typically on a table. The table is axially movable within the central opening so that the patient may be positioned at various locations enabling respective slices to be obtained at multiple axial positions. Each of the slices obtained is then processed in a computer to produce enhanced images that are useful for diagnoses and inspection.

The rotating frame typically includes an x-ray source, a detector array and electronics necessary to generate image data for each view. An electronics system, typically stationary, is employed to process raw image data. It is thus necessary to communicate image data between the rotating frame and the electronic system for image processing.

The rate of data communication between the stationary electronic system and the gantry is important because the rate affects the speed at which the images can be processed. It is desirable to obtain image views as fast as possible to maximize image quality, reduce patient discomfort, and to maximize equipment utilization. In current CT systems, a single view typically comprises about 800 detector channels with a 16 bit representation for each individual detector channel and is typically repeated one thousand times per second, yielding a net data rate of about 13 million bits per second (Mbit/sec) for image data. Advanced CT systems capable of simultaneously constructing multiple image slices by employing four, eight, sixteen, or more times as many detector channels, will increase the required data rate to the hundreds of mega-bits per second range.

Prior CT systems have employed brushes, slip rings, and radio frequency links for communicating the image data between the rotating frame and the stationary frame. CT systems utilizing brushes and slip rings for communications have generally suffered significant limitations in data transfer rates due to the substantial time required to propagate the signals around the circular slip rings. At the desired data rates, the electrical path length around the rings is an appreciable fraction of the data bit transfer period so that electromagnetic waves propagating around the rings in the opposite direction may arrive at the reception point at substantially different times within the bit transfer period causing signal interference.

Additionally, radio frequency communication links, historically, have not been able to achieve the very high data transfer rates required of future CT systems at reasonable costs. Radio frequency links typically are more expensive to produce as the data rate increases because of the electromagnetic emissions requirements that must be met. As such, it is desirable to employ a CT communications link between the stationary electronics and rotating electronics that can operate with very high data rates without causing interference with other equipment.

It is also desirable to provide a communication link between the stationary frame and the rotating frame that is immune to electromagnetic radiation interference such as is typically produced in a hospital environment by cellular telephones, defibrillating devices, surgical saws, and electrical noise produced by any given CT system.

Current optical rotary links are expensive. One type uses lenses, mirrors, or many emitters and detectors to insure continuous optical communication at any gantry angle. Such systems require expensive alignment. Another type of rotary link uses an "optical brush" that contacts an optical transmission line with sufficient force to deform the line. At the deformity the high data rate optical data signal can enter (or exit) the line at such an angle as to be captured within the transmission line (total internal reflection) and then propagate, unimpeded, to a detector disposed at the end of the transmission line. This then provides a mechanism for coupling an externally generated high data rate optical data signal into the line at any point along the transmission line (at any gantry angle). The deformation point, however, moves along the transmission line as the gantry rotates and this process eventually causes the transmission line and coupler to wear, resulting in failure.

Yet another type of rotary optical link uses a transmission line that is doped with a dye that becomes temporarily luminescent when irradiated with laser light. The luminescent radiation is from inside the optical transmission line and a portion of this optical data signal is at such an angle as to be captured within the transmission line. Existing dyes have a response that is too slow to support the desired high data rate. Furthermore, the dyes eventually degrade.

Finally, another type of rotary link uses an optical transmission line, for example, a fiber that is heat treated to create many small fractures. Each fracture scatters high data rate optical data signal at such an angle as to be captured within the line. With this approach, the treated fiber is very small and brittle, and the coupling and propagation losses are high. In many of the above approaches, there is a dead spot or gantry angle where communication is not supported.

Accordingly, there is a need in the art for an improved communications link for CT x-ray machines.

SUMMARY OF THE INVENTION

A computed tomography system employs an optical communications link to reliably transmit high data rate data. The communications link comprises an optical emitter, an optical transmission line comprising at least two sections, a plurality of optical deflectors disposed randomly within the transmission line, and an optical receiver. The optical emitter is attached to the gantry of the computed tomography system and extends along the length of the gantry. The optical emitter generates a high data rate optical data signal, which travels along the optical transmission line in correspondence with data generated by detector array on the gantry. The plurality of optical deflectors causes portions the high data rate optical data signal to be internally reflected and subsequently refracted from the transmission line. The optical receiver disposed near the transmission line detects the portion of high data rate data refracted from the transmission line.

DETAILED DESCRIPTION OF THE INVENTION

Figure 1:
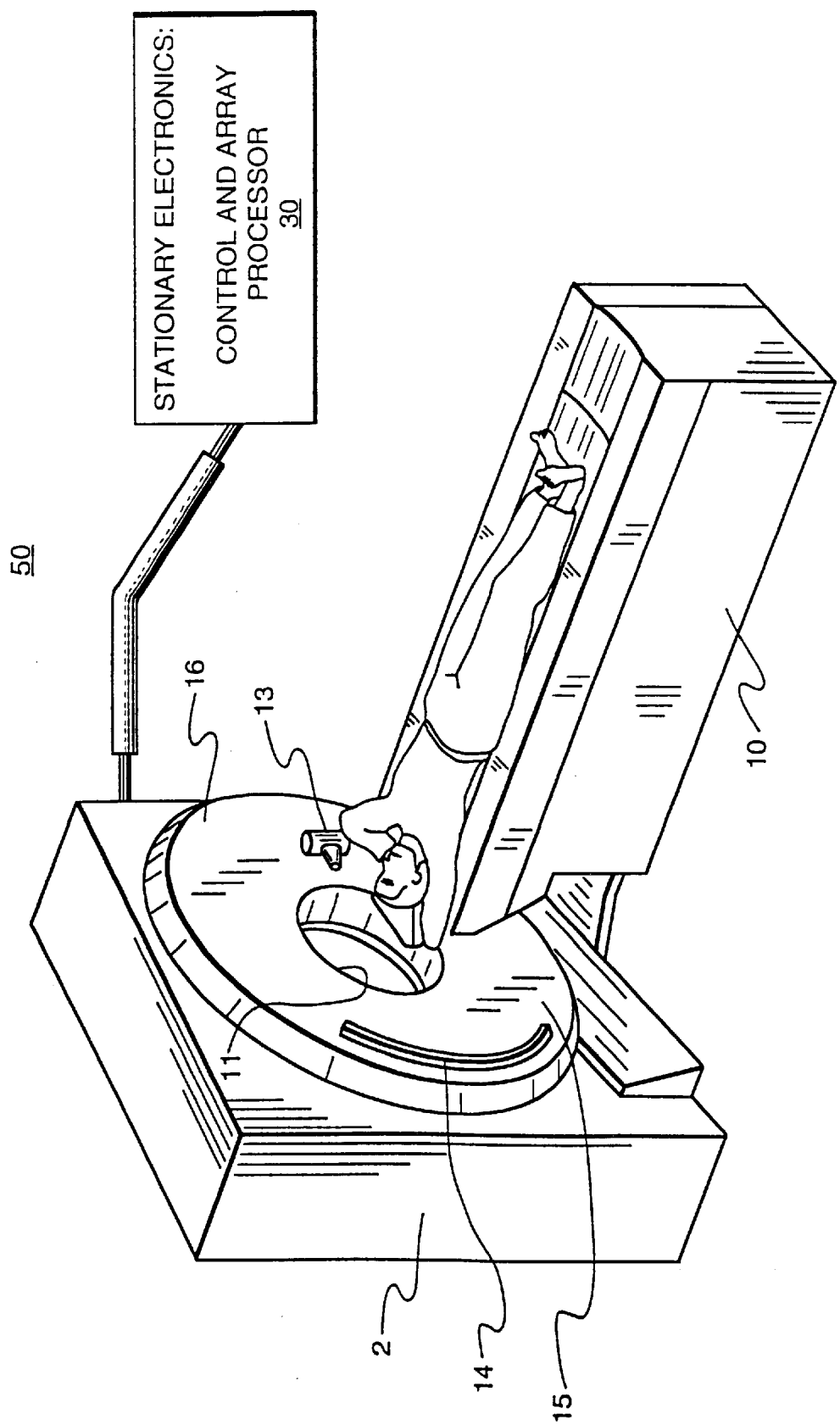
FIG. 1 is a conventional computed tomography system having a gantry and stationary electronics.

A computed tomography (CT) system 50, typically employs a CT base 2, a source of imaging energy 13, a detector array 14, an annular rotating gantry 15 having an outer circumference 16, and a stationary electronics system 30 to obtain multiple x-ray images of a patient or object, as shown in FIG. 1.

Detector array 14 comprises a plurality of detectors, for example, several thousand detectors, which detectors generate x-ray data that is utilized to simultaneously construct multiple image slices. Detector array 14 is typically mechanically coupled to gantry 15 and rotates therewith. In one embodiment, gantry 15 is about four (4) feet in diameter and rotates at about 2 revolutions per second.

A patient or object is generally positioned in or near a central aperture 11 of gantry 15 on a table that is axially movable along base 2, enabling respective x-ray slices to be obtained at multiple axial positions. The x-ray slices are processed at stationary electronics systems 30 to produce enhanced images for diagnoses or inspection.

Figure 2:
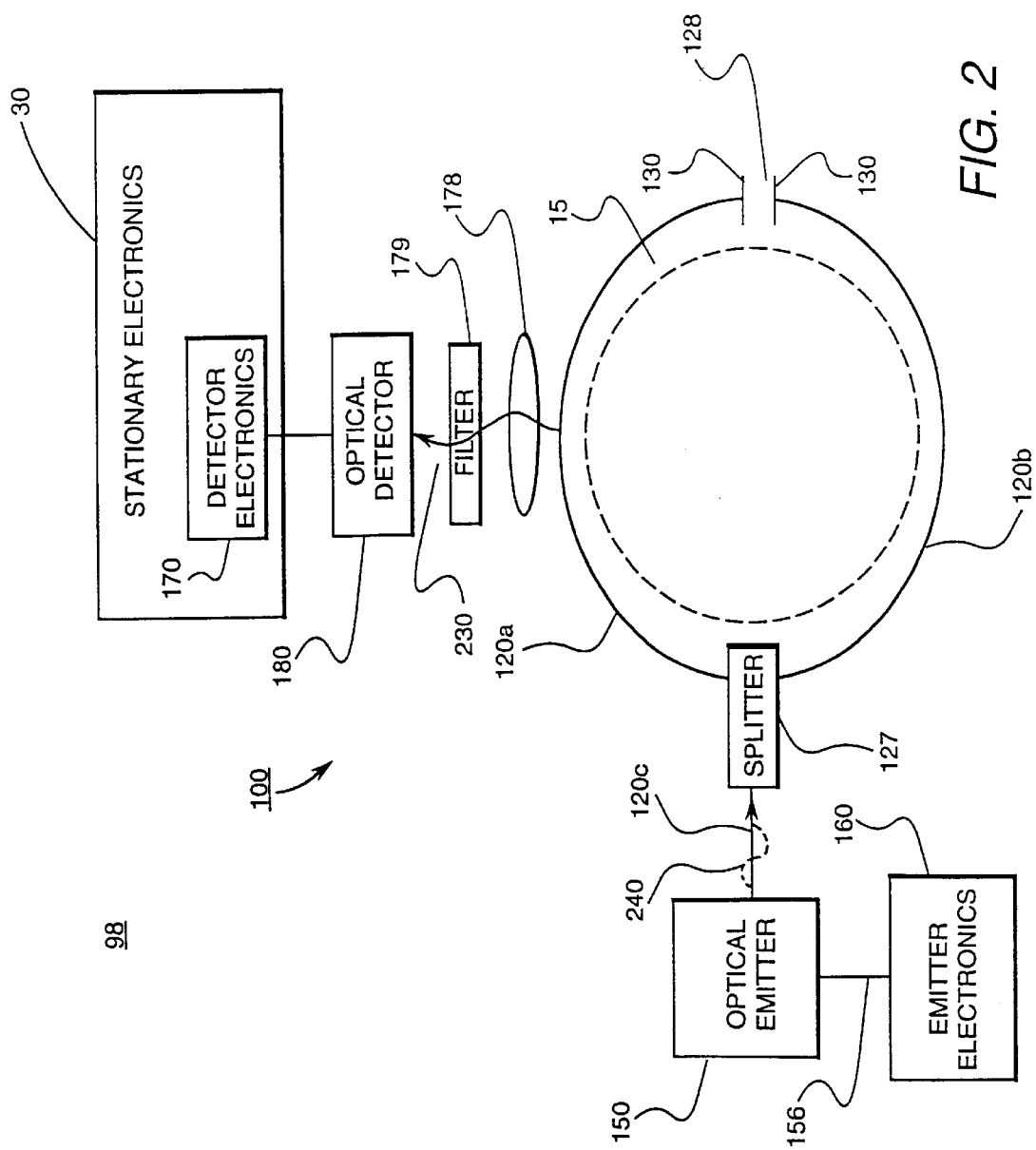
FIG. 2 is a functional block diagram of one embodiment of a communications link of the present invention coupled to a gantry of a computed tomography system.

In accordance with the instant invention, an optical communications link 100 is employed in a CT system 98 to transmit detector array data from gantry 15 to stationary electronics 30, as shown in FIG. 2.

In one embodiment of the present invention optical communications link 100 comprises an optical transmission line 120 that is disposed about the circumference of gantry 15, an optical emitter 150 coupled to a first end of optical transmission line 120, and a stationary optical detector 180 disposed adjacent to transmission line 120.

Optical emitter 150, for example, a light emitting diode or a laser diode, is modulated with binary data 156, generated by detector array 14, and produces a high data rate optical data signal 240, which high rate signal 240 is transmitted through transmission line 120.

Stationary optical detector 180 is positioned adjacent transmission line 120 to detect a portion of high rate signal 240 refracted outside of transmission line 120, which portion is termed a refracted signal 230.

Optical transmission line 120 typically comprises two, generally, semi-circular segments, each optically coupled at a first end with optical emitter 150 for receiving high rate signal 240 and at a second end with an optical absorber 130, which optical absorber 130 minimizes internal reflections of high rate signal 240.

Figure 3:
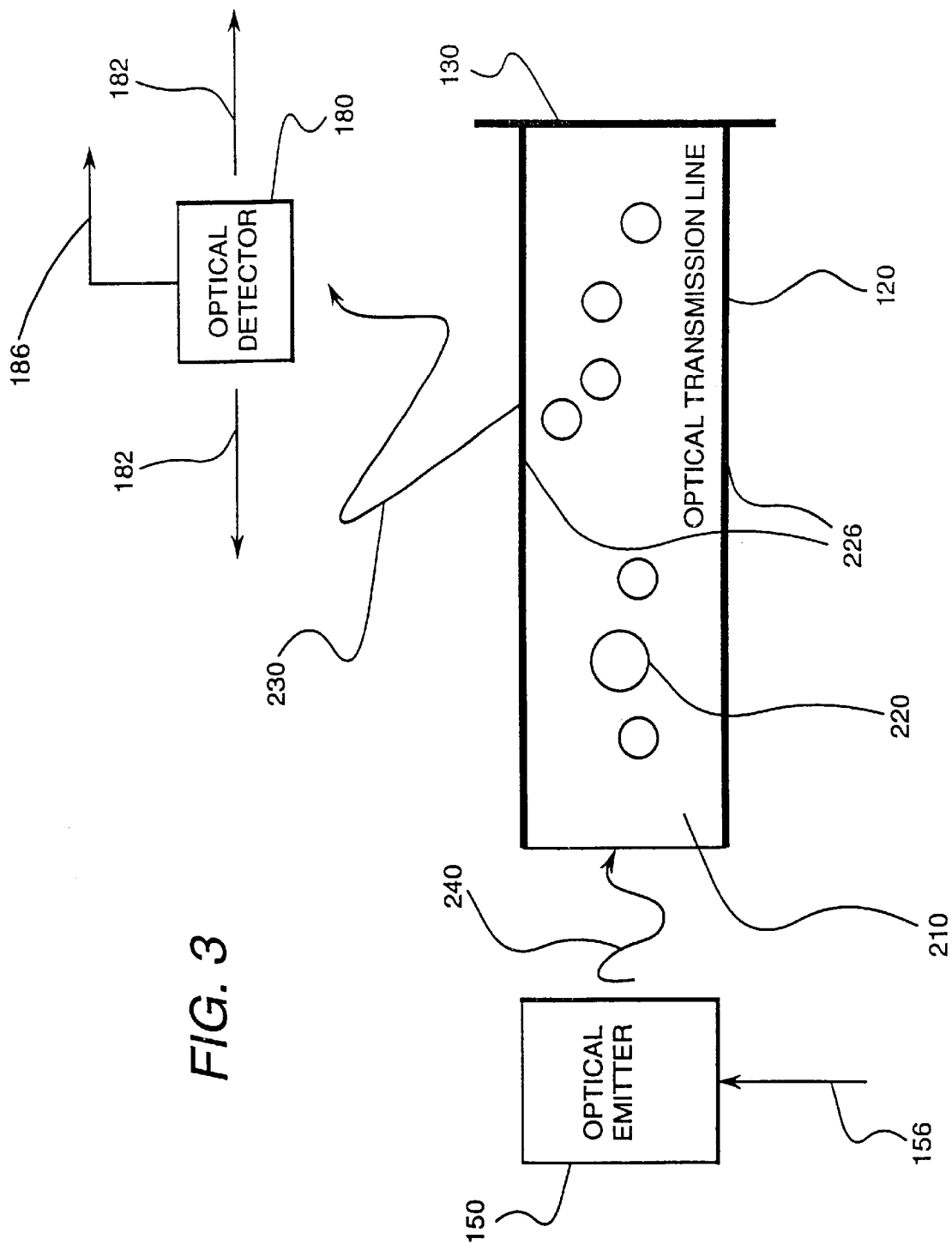
FIG. 3 is a block diagram illustration of one embodiment of a communications link employing translucent bubbles to generate a scattered data signal.

In one embodiment, transmission line 120 is made of glass, plastic, or other translucent polymeric material. Transmission line 120 further comprises internal light scatter(s) 220, for example bubbles, to redirect portions of high rate signal 240, as shown in FIG. 3. Internal light scatters 220 redirect portions of high rate signal 240 to an outer surface 226 of transmission line 120 such that a portion of high rate signal 240 escapes transmission line 120. The escaping refracted signal 230 is then detected by optical detector 180. The non-escaping portions of high rate signal 240 propagate through transmission line 120 and are absorbed by optical absorber 130.

High data rate optical data signal 240 comprises x-ray data generated by detector array 14. The x-ray data comprises both image and control information. In the present example, the x-ray data corresponds with image data and communication protocol data generated by CT system 50. The x-ray data may, for example, be pulse width modulated or frequency modulated. The data rate of the x-ray data may be in the Giga-Hertz range, and is typically from about 10 mega-Hertz to about 10 Giga-Hertz. The information content of optical data signal 240 is also present in refracted optical data signal 230, as such, the information content of optical data signal 240 is coupled to optical detector 180 during the communication process of the present invention.

In another embodiment, transmission line 120 is constructed using ⅛ inch diameter plastic rod with an index of refraction of about 1.5. During manufacture, the plastic rod may be drawn through an orifice where small air bubbles are injected before the rod completely solidifies. The air flow is adjusted to entrain approximately 10 bubbles per inch of line length, with the bubbles being approximately 0.01 inches in diameter. The density and size of bubbles 220 is adjusted so that, for each 1 inch section of transmission line 120, approximately 5% of the power in the optical data signal 240 is refracted by bubbles 220 to become refracted optical data signal 230. This yields an exponential decay of signal power along the line, with approximately 50% of the power remaining at the end of a 12-inch line section.

Figure 4:
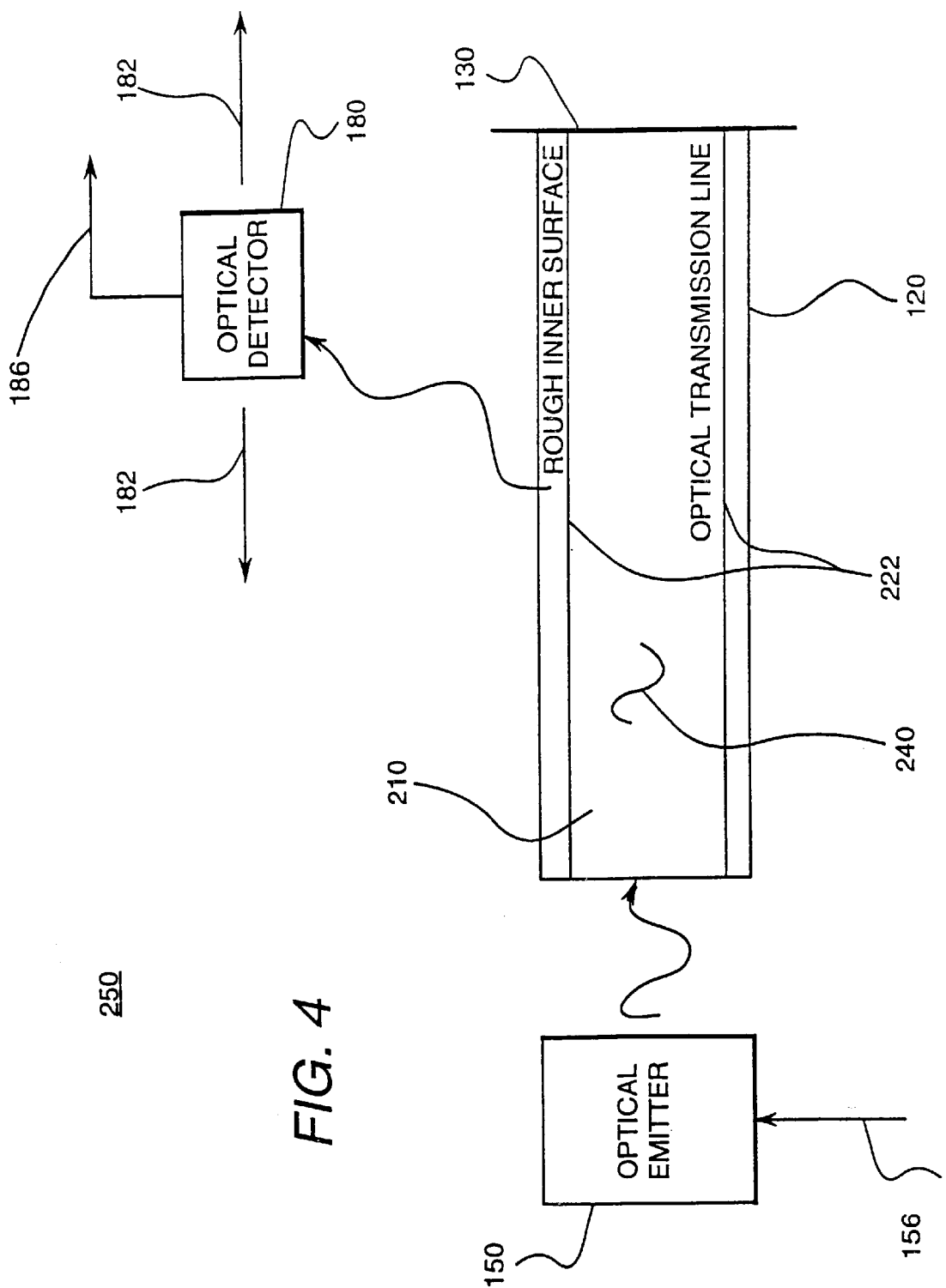
FIG. 4 is a block diagram illustration of one embodiment of a communications link employing a transmission line with a rough inner cladding surface.

A further exemplary embodiment of the present invention is illustrated in FIG. 4. In this embodiment transmission line 120 comprises a hollow tube, or alternatively, translucent waveguide material 210. An inner surface 222 of the tube is etched to give it a roughness for scattering high data rate optical data signal 240. Waveguide material 210 has a dielectric constant that is different from the dielectric constant of the material having inner surface 222. Optical data signal 240 propagates within waveguide core material 210. Optical data signal 240 scatters after colliding with rough inner surface 222. Waveguide core material 210 additionally comprises, for example, clear plastic, a gas, a clear liquid, or the like.

Figure 5:
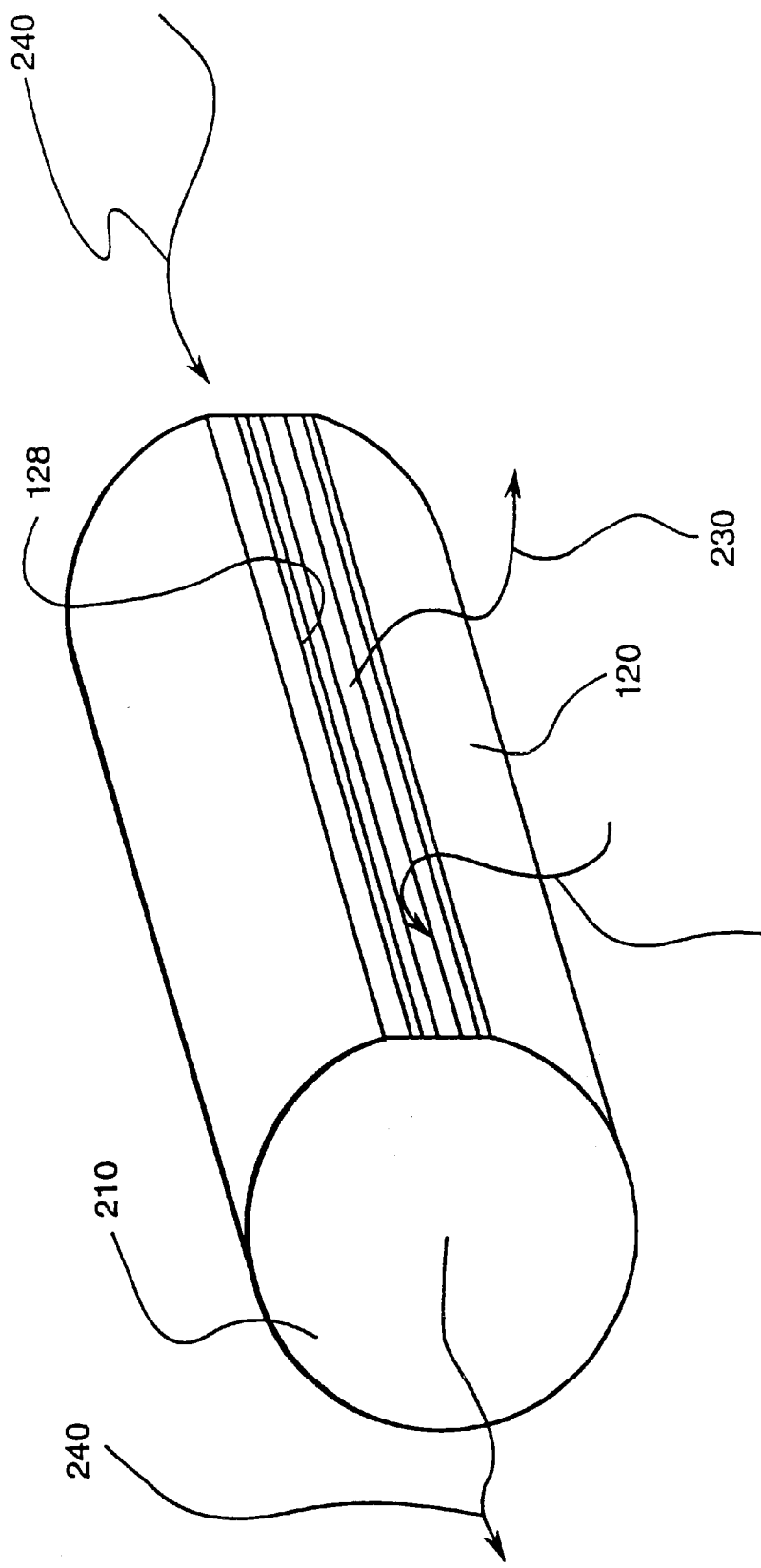
FIG. 5 is an illustration of a transmission line having a rough portion of the outer surface area.

In another embodiment, transmission line 120 comprises a waveguide core material 210 having a coarse portion of an outer surface and smooth portions of an outer surface. The coarse portions of outer surface provide a breach of the total internal reflection condition to redirect portions of high rate signal 240 to escape transmission line 120, as shown in FIG. 5.

As an example, a 0.25-inch diameter plastic rod is used as the radiating transmission line section. To break the TIR condition and allow some radiation, a single rough stripe is established along the length of the line section. The surface roughness along the stripe may be approximately 1 mil root-mean square (surface height variation).

The stripe width is approximately 0.125 inches, or equivalently span approximately 1 radian of the circumference.

In a further embodiment of the instant invention, a control signal 231 is directed into transmission line 120 at course portion(s) 128 to enable bi-directional communication.

Figure 6:
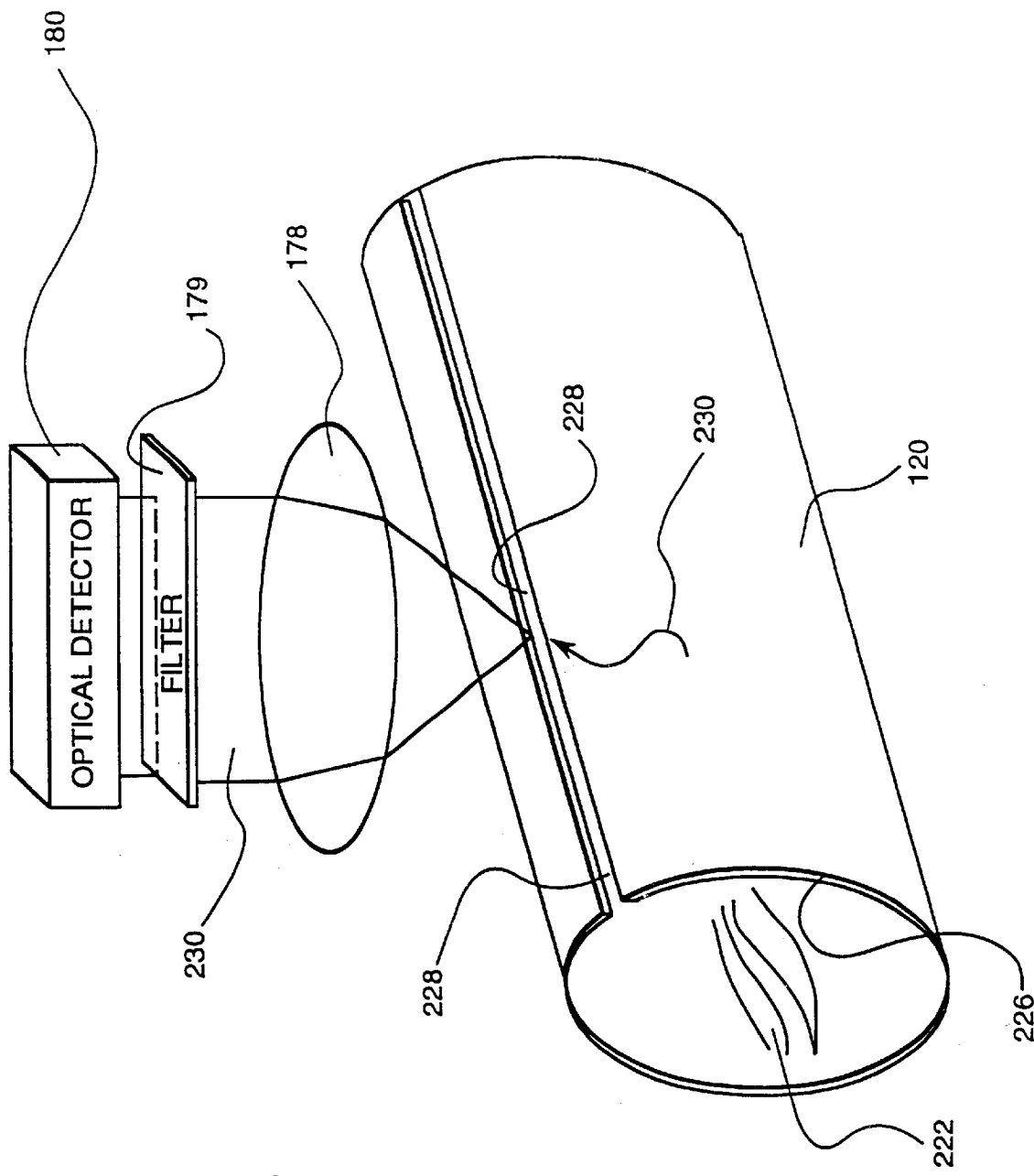
FIG. 6 is a block diagram illustration of a lens focused optical detector of the present invention.

In another alternative embodiment, transmission line 120 comprises a reflective outer surface, as shown in FIG. 6. Transmission line is encapsulated with a reflective cladding 226, for example, aluminum. An aperture 228 is disposed along the axial length of transmission line 120. Aperture 228 may alternatively comprise a plurality of intermittently spaced narrow slits.

Optical detector 180 utilizes a lens 178 and a filter 179 to collect refracted signals 230 from transmission line 120. Aperture 228 is sized to enable a portion of high rate signal 240 to escape from transmission line 120 so as to be detected by optical detector 180. The width of aperture 228 is in the range between about 1/10 to about 1/100 of the circumference of transmission line 120.

Figure 7:
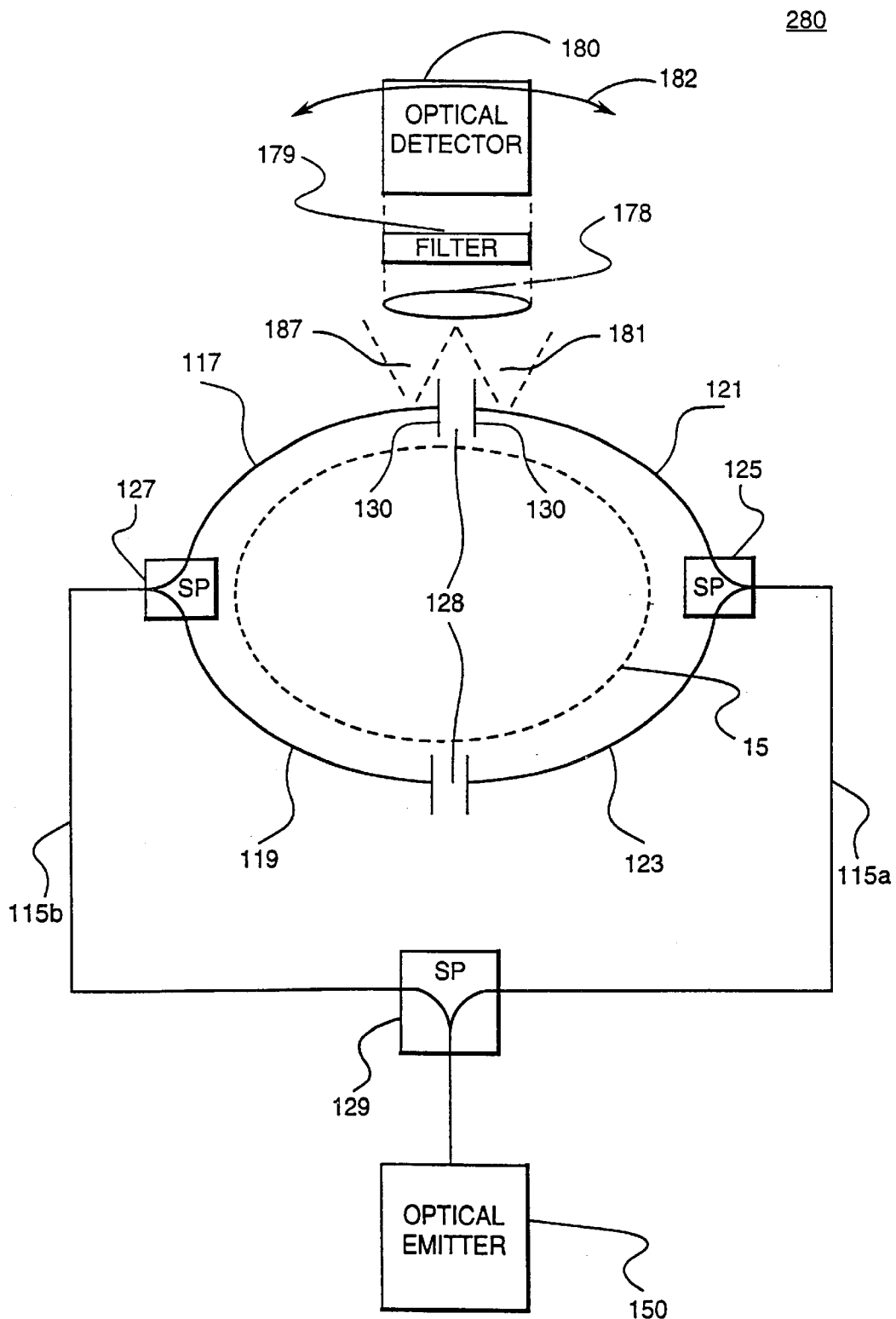
FIG. 7 is a block diagram illustration of a multi-segment communications link.

In accordance with another embodiment of the instant invention, a sub-divided transmission line 120 is shown in FIG. 7. Subdivision of transmission line 120 provides shorter lengths for each transmission line section. This reduces the worst case delay dispersion in each transmission line section. The data rate of high rate signal 240 can be, correspondingly, increased as the delay dispersion of high rate signal 240 is reduced. To allow reliable data communication, the delay dispersion in refracted optical data signal 230 at any detector position should be such that the eye pattern is substantially open, as is well known by one skilled in the art. For example, for a data rate of 1.0 Gigabit/second and binary (on-off) signaling, approximately 90% of refracted optical data signal 230 reaching the detector should have a time dispersion of less than ±0.125 nano-seconds (nsec). In order to reduce delay dispersion in transmission line 120, transmission line 120 is subdivided into a plurality of subsections.

One embodiment is illustrated in FIG. 2 in which transmission line 120 is subdivided into two generally equal subsections 120a, 120b. Subsections 120a, 120b are each optically coupled at a first end to a splitter 127 and at a second end to optical absorber 130. An additional section 120c may be utilized to optically couple high rate signal 240 to splitter 127.

In communications link 100, as gantry 15 is rotated and detector 180 moves away from splitter 127 along transmission line 120, the data communication delay increases until optical detector 180 is disposed adjacent optical absorber 130. As rotation continues, the delay then decreases until detector is again disposed adjacent to splitter 127.

In an alternative embodiment, illustrated in FIG. 7, transmission line 120 is subdivided into four subsections (117, 119, 121, and 123, respectively), so as to reduce the delay dispersion in transmission line 120.

It is preferable that high rate signal 240 arrive at any two ends of transmission line 120 adjacent to a given gap 128 at substantially the same time, less than about 0.125 nsec. For example, when communicating with binary signaling at 1.0 Gigabits/second, the optical data signal 240 at any two adjacent ends of transmission line 120 should be time aligned within about ±0.125 nsec. That is, the leading edge of a single on-off transition at the output of the laser diode should arrive at the two sides of a respective gap 128 within ±0.125 nsec. For transmission line material that has an index of refraction of about 1.5, the propagation speed is about 1.5 nsec/foot and the two optical paths lengths to an associated gap should be within about 1 inch of each other in order to achieve a time alignment of ±0.125 nsec.

In operation, high rate signal 240 is generated by optical emitter 150 and traverses along four paths of transmission line 120. In a first path, high rate signal 240 is split by a first splitter 129 and travels through a section 115b, is split by a second splitter 127 and travels through section 117 to an optical absorber 130. In a second path, high rate signal 240 is split by first splitter 129 and travels through a section 115a, is split by a third splitter 125 and travels through section 121 to optical absorber 130. In a third path, high rate signal 240 is split by first splitter 129 and travels through section 115b to second splitter 127 and travels through section 119 to optical absorber 130. In a fourth path, high rate signal 240 is split by first splitter 129, and travels through section 115a to third splitter 125, and travels though a section 123 to optical absorber 130. In this embodiment the length of each path is substantially equal. Each path length is selected such that high rate signal 240 arrives at each optical absorber 130 at substantially the same time, typically about ±0.125 nsec apart.

Accordingly, in this embodiment, two portions of a respective high rate signal 240 arrive at respective optical absorbers 130, adjacent to a respective gap 128, at substantially the same time. Further, a refracted signal 181 radiating from a first side of gap 128 is also in time alignment with a refracted signal 127 radiated from a second side of gap 128.

Consequently, detector 180 receives refracted signals 181, 187 at substantially the same time. Accordingly, in this embodiment, inter-symbol interference is minimized when detector 180 is disposed adjacent to gap 128, and "dead spots" are minimized in transmission line 120. As used herein, inter-symbol interference is the interference between time adjacent symbols transmitted on a communication channel. The signal, voltage, current, etc. associated with the symbol transmitted at one time must decay sufficiently so as not to have a substantial residual during the transmission time for the following symbol. The residual level, relative to the desired symbol level, is a measure of the inter-symbol interference. As used herein, the phrase "dead spot" is defined as a portion of transmission line in which optical detector 180 cannot detect a refracted signal.

Figure 8:
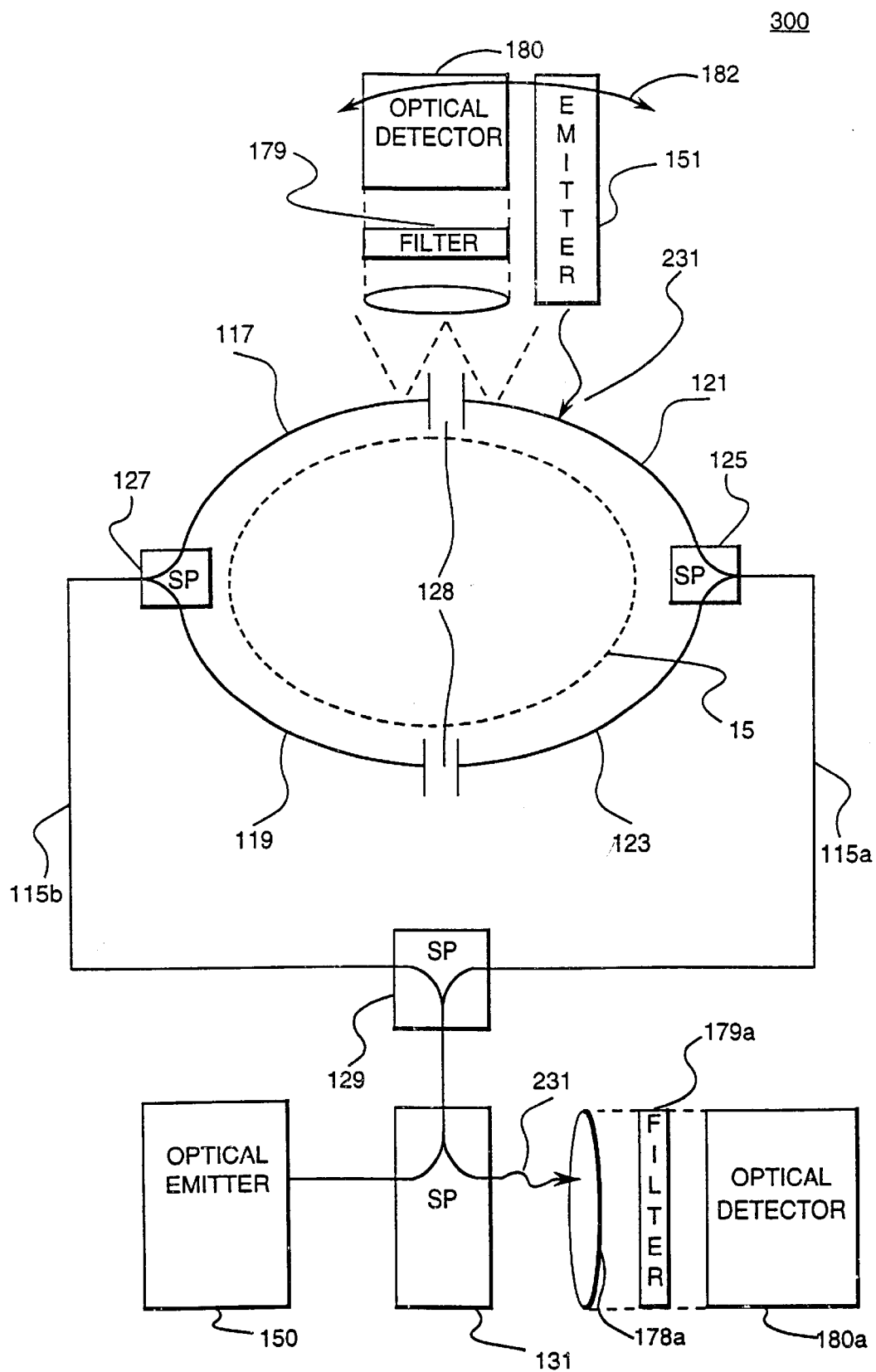
FIG. 8 is a block diagram illustration of a multi-segment bi-directional communications link.

In a further exemplary embodiment of the present invention an additional optical emitter 151 is employed in communications link 300 to enable bi-directional communications, as is illustrated in FIG. 8. Optical emitter 151 is disposed sufficiently close to transmission line 120 to couple data control optical signal 231 into transmission line 120. Emitter 151 is thus adapted to enjoy relative movement with respect to transmission line 120 along a path 182. A second optical detector 180a is also employed and is coupled to transmission line 120 so as to detect control data signal 231. Control data signal 231 traverses section 121, passes through splitter 125, traverses through section 115a, passes through splitter 129 and a splitter 131. Control data signal 231 is then focused by lens 178a, filtered by filter 179a, and detected by detector 180a. Data may thus be coupled from optical emitter 150 to detector 180 and, additionally, control data signal 231 may be coupled from emitter 151 to detector 180a. It is to be understood that control signal 231 may also comprise data.

It will be apparent to those skilled in the art that, while the invention has been illustrated and described herein in accordance with the patent statutes, modifications and changes may be made in the disclosed embodiments without departing from the true spirit and scope of the invention. It is, therefore, to be understood that the appended claims are intended to cover all such modifications and changes as fall within the true spirit of the invention.

What is claimed is:

1. An optical communications link to reliably transmit a high data rate optical data signal over said optical link, said optical link comprising:

an optical transmission line comprising at least two transmission line sections, wherein each transmission line section has at least one end;

wherein each said respective transmission line section is disposed so that said respective end is adjacent to an end of an adjacent one of said transmission line sections, so that there is a gap between each of said two respective adjacent ends;

an optical emitter being coupled to each of said transmission line sections, wherein said optical emitter is adapted to simultaneously generate said high data rate optical data signal within each one of said transmission line sections so that said optical data signal traverses within each of said transmission line sections and arrives at the ends of each section at substantially the same time period;

refractors within each of said transmission line sections for generating a radiated portion of said optical data signal that exits said transmission line at any point along the length of said transmission line; and an optical detector for detecting the radiated portion of said optical data signal.

2. The optical communications link as recited in claim 1, wherein said respective transmission line section has a length that is selected to be sufficiently short to reduce delay dispersion of said optical data signal.

3. The optical communications link as recited in claim 2, wherein each of said respective transmission line sections has a respective length that is selected so that said optical data signal is in time alignment at said respective gap.

4. The optical communications link as recited in claim 3, wherein each of said respective transmission line sections has a respective length that is substantially equal so that said optical data signal is in time alignment at said respective gap.

5. The optical communications link as recited in claim 1, further comprising a respective absorber coupled to a respective end of said transmission line section, wherein said respective absorber is adapted to minimize reflections of said optical data signal.

6. The optical communications link as recited in claim 1, wherein said optical detector is adapted to have relative movement with respect to said transmission line, so that said optical detector may detect the radiated portion of said optical signal at any point along the length of said transmission line.

7. The optical communications link as recited in claim 1, further comprising a respective lens coupled to said optical detector to focus the radiated portion of said optical signal onto said optical detector.

8. The optical communications link as recited in claim 1, further comprising a respective optical filter coupled to said optical detector to filter unwanted optical signals.

9. The optical communications link as recited in claim 1, wherein said communications link is adapted to concurrently communicate optical data bi-directionally within said transmission line.

10. The computed tomography system as recited in claim 1, wherein said transmission line comprises a plurality of sections.

11. A computed tomography system employing an optical communications link to reliably transmit at least one high data rate optical data signal over said optical link, said computed tomography system having a rotating gantry and a detector array coupled to the gantry, said computed tomography system comprising:

at least one optical emitter being coupled to the gantry, wherein said optical emitter is adapted to generate a respective high data rate optical data signal in correspondence with data generated by the detector array;

an optical transmission line being coupled to the gantry of said computed tomography system, said optical transmission line comprising at least two transmission line sections, wherein said respective transmission line section has at least one end, wherein said respective transmission line section is coupled to said respective optical emitter so as to receive said respective optical data signal;

a plurality of deflectors disposed within each of said respective transmission line sections, wherein said plurality of deflectors is adapted to generate a respective refracted portion of said respective optical data signal at any point along the length of said transmission line section; and wherein each of said respective transmission line sections is disposed so that said respective end is adjacent to an end of an adjacent one of said transmission line sections, so that there is a gap between any said two respective ends of said respective transmission line section.

12. The computed tomography system as recited in claim 11, wherein said respective transmission line section has a length that is selected to be sufficiently short to reduce delay dispersion of said respective optical data signal.

13. The computed tomography system as recited in claim 12, wherein each of said respective transmission line sections has a respective length that is selected so that said respective optical data signal is in time alignment at said respective gap.

14. The computed tomography system as recited in claim 13, wherein each of said respective transmission line sections has a respective length that is substantially equal so that said respective optical data signal is in time alignment at said respective gap.

15. The computed tomography system as recited in claim 11, further comprising a respective absorber coupled to each respective end of said transmission line section, wherein said respective absorber is adapted to minimize reflections of said respective optical data signal.

16. The computed tomography system as recited in claim 11, further comprising an optical detector, wherein said optical detector is adapted to have relative movement with respect to said transmission line, so that said optical detector may detect the radiated portion of said respective optical signal at any point along the length of said transmission line.

17. The computed tomography system as recited in claim 16, further comprising a respective lens coupled to said optical detector to focus the radiated portion of said respective optical signal onto said optical detector.

18. The computed tomography system as recited in claim 16, further comprising a respective optical filter coupled to said optical detector to filter unwanted optical signals.

19. The computed tomography system as recited in claim 11, wherein said communications link is adapted to concurrently communicate optical data bi-directionally within said transmission line.

20. The computed tomography system as recited in claim 11, wherein said transmission line comprises a plurality of sections.

* * * * *